(12) United States Patent
Nehls

(10) Patent No.: US 9,179,946 B2
(45) Date of Patent: Nov. 10, 2015

(54) LOW-PROFILE ANTERIOR VERTEBRAL PLATE ASSEMBLIES AND METHODS OF USE

(76) Inventor: Daniel Nehls, Tacoma, WA (US)

(*) Notice: Subject to any disclaimer, the term of this patent is extended or adjusted under 35 U.S.C. 154(b) by 504 days.

(21) Appl. No.: 12/881,158

(22) Filed: Sep. 13, 2010

(65) Prior Publication Data

US 2012/0065688 A1 Mar. 15, 2012

(51) Int. Cl.
| | | |
|---|---|---|
| *A61B 17/70* | (2006.01) | |
| *A61B 17/88* | (2006.01) | |
| *A61F 2/44* | (2006.01) | |
| A61B 17/80 | (2006.01) | |
| A61F 2/30 | (2006.01) | |

(52) U.S. Cl.
CPC ......... *A61B 17/7077* (2013.01); *A61B 17/7059* (2013.01); *A61F 2/44* (2013.01); *A61B 17/70* (2013.01); *A61B 17/8004* (2013.01); *A61B 17/8061* (2013.01); *A61F 2/4455* (2013.01); *A61F 2002/30471* (2013.01); *A61F 2002/30576* (2013.01); *A61F 2002/30578* (2013.01); *A61F 2002/30785* (2013.01); *A61F 2002/30787* (2013.01); *A61F 2002/30789* (2013.01); *A61F 2002/444* (2013.01); *A61F 2310/00011* (2013.01); *A61F 2310/00017* (2013.01); *A61F 2310/00023* (2013.01); *A61F 2310/00161* (2013.01)

(58) Field of Classification Search
CPC ............... A61B 17/80; A61B 17/8004; A61B 17/8023; A61B 17/8061; A61B 17/885; A61B 17/7059; A61B 17/70; A61B 17/7061; A61B 17/7062; A61B 17/7071; A61B 17/7094; A61B 17/8028; A61B 17/8033; A61B 17/8038; A61B 17/8042; A61B 17/8047; A61B 17/8052; A61B 17/8057; A61B 17/8066; A61B 17/8071; A61B 17/8076; A61B 17/808; A61F 2/44; A61F 2002/4435
USPC .................................................. 606/280–299
See application file for complete search history.

(56) References Cited

U.S. PATENT DOCUMENTS

| | | | | |
|---|---|---|---|---|
| 4,759,769 | A | * | 7/1988 | Hedman et al. ............. 623/17.13 |
| 5,562,738 | A | * | 10/1996 | Boyd et al. ................. 623/17.15 |
| 6,599,292 | B1 | | 7/2003 | Ray |
| 2003/0229348 | A1 | | 12/2003 | Sevrain |
| 2005/0113927 | A1 | * | 5/2005 | Malek ......................... 623/17.16 |
| 2006/0030943 | A1 | * | 2/2006 | Peterman ................... 623/17.11 |
| 2006/0069442 | A1 | * | 3/2006 | Michelson .................. 623/17.15 |
| 2008/0195158 | A1 | | 8/2008 | De Villiers |
| 2008/0228230 | A1 | | 9/2008 | Ferree |
| 2009/0270927 | A1 | * | 10/2009 | Perrow et al. ................. 606/286 |
| 2009/0326589 | A1 | | 12/2009 | Lemoine |

* cited by examiner

*Primary Examiner* — Kevin T Truong
*Assistant Examiner* — Tracy Kamikawa
(74) *Attorney, Agent, or Firm* — Baumgartner Patent Law; Marc Baumgartner

(57) ABSTRACT

Low-profile anterior vertebral plate assemblies and methods of use are disclosed herein. The plate assemblies herein are useful for coupling adjacent vertebral bodies together. Preferred vertebral plates assemblies herein are low-profile, meaning that the assemblies herein are positioned partially within and partially outside of the intervertebral space. Additional teachings are directed to hinged low-profile anterior vertebral plate assemblies that allow slight flexion towards the vertebral bodies in a sufficient amount to prevent kyphosis, and encourage a desired amount of lordosis.

16 Claims, 9 Drawing Sheets

LOW-PROFILE ANTERIOR VERTEBRAL PLATE ASSEMBLIES AND METHODS OF USE

FIELD OF THE INVENTION

The embodiments herein relate to low-profile anterior vertebral plates and methods of use in spinal fixation procedures. More particularly, the teaching herein relate to improving current methods and systems directed to fusing one or more adjacent vertebrae.

BACKGROUND

The spine consists of a series of bone structures termed "vertebrae." Between each vertebra is a flexible, connective tissue termed an "intervertebral disc" which secures one vertebrae to another and functions as a shock absorber. Spinal fixation is a surgical technique in which one or more vertebrae are joined by an implant (e.g., a plate or rods.) to prevent relative movement of the spine, with the goal of live bone eventually fusing the adjacent vertebrae together.

Patients requiring spinal fusion typically suffer from either neurological deficits or severe pain which has not responded to conservative treatment. Typical conditions that are treated by spinal fusion procedure non-exclusively include: degenerative spinal conditions, discogenic pain, spinal tumor, vertebral fracture, scoliosis, kyphosis, spondylolisthesis, spondylosis, and other conditions that causes instability or pain in the spine.

Typically a spinal fixation procedure does not connect the patient's original vertebrae directly together; rather the intervertebral disc is usually completely or partially removed (disectomy) and/or one or more entire vertebral bodies are removed (corpectomy). The space remaining from the removed discs and vertebral bodies after a disectomy or corpectomy is typically replaced by a graft positioned between adjacent vertebrae to maintain proper length in the spinal column. After the surgery, it is desirable to have the living bone from the vertebrae span the inter-body graft thereby fusing the adjacent vertebrae together.

Traditionally, interbody grafts are fashioned from bone taken from a patient's skeleton, and are also referred to as "autografts." As the harvesting of an autograft is painful for the patient, many surgeons now prefer the use of "allografts" which are harvested from a body other than the patient's. Interbody grafts may also be formed from synthetic materials such as titanium, carbon fiber and plastics. Unfortunately, grafts are associated with a relatively high rate of dislodgement due to the patient's neck movement during the healing process. To minimize the risk of dislodgement of the interbody graft posteriorly, toward the spinal cord, surgeons routinely mortise the graft by drilling a shelf into the vertebrae. To minimize the risk of dislodgement of the interbody graft anteriorly, surgeons routinely place a fusion plate across the inner space and secure it with screws extending into the vertebrae.

Placement of an anterior cervical plate with screw fixation is effective in preventing interbody graft dislodgement toward the esophagus and also enhances fusion by providing fixation between the vertebrae. In general, a cervical plate is attached to the anterior cortex of the vertebrae. This method can be disadvantageous as these plates are generally not low-profile, not easily compressible, nor easily centered. Cervical plates also tend to be long and may encroach upon the space of an adjacent disc space or vertebral body. Alternatively, other spinal devices are configured to be inserted directly into the disc space and attach to the vertebral endplates. This approach also is disadvantageous in that attachment to the vertebral endplates is not as strong as attachment to the hard anterior cortex of the vertebrae.

An additional problem of prior art plates is that their rigid attachment to the vertebral bodies can prevent compressive forces on the vertebral bodies, which in turn can prevent proper fusion of the graft. In attempt to counter this problem, new plate designs were developed that used slotted holes for the screws, configured such that the screws could slide in the slots, allowing compression of the graft. At least two problems are associated with these plates. Firstly, as the front of the spine compresses, compression in the back is limited by the facet joints posteriorly, which causes an abnormal forward angulation and flexion called kyphosis. Secondly, as the screws move down in the plate slots as the graft is compressed, the inferior and superior portions of the plate can encroach upon the neighboring disc areas or vertebral bodies, above and below the compressed vertebral bodies, and lead to advanced degeneration. In an attempt to counter the encroachment issue, new plates were designed that shorten when compressed. While addressing the encroachment problem, the shortening or translating plates can still lead to kyphosis as shown in FIG. 7. Stated otherwise, anterior vertebral plates that shorten in length when the graft and the surrounding vertebral bodies are compressed can still lead to the anterior area of the disc space collapsing more so than the posterior area.

Accordingly, there is a need in the art for improved spinal plates that are lower profile, more easily compressible and centered, do not encroach upon the space of a nearby disc or vertebral body, and that attach to bone that is stronger than the vertebral endplates. Additionally there is a need for anterior vertebral plates that prevent kyphosis, or forward angulation, of the spine and encourages the natural lordotic, or inward curvature, of cervical and lumbar regions of the vertebral column.

SUMMARY OF THE INVENTION

Embodiments herein are directed to vertebral plate assemblies adapted to be permanently implanted partially within an intervertebral space between superior and inferior vertebral bodies having anterior cortex faces and vertebral endplates, and comprising a posterior surface configured to fit within the intervertebral space and an anterior surface that is configured to be external to the intervertebral space after being implanted; a plurality of anchor members coupled to the anterior surface wherein the plurality of anchor members are configured to abut against the anterior cortex faces of the superior and inferior vertebral bodies when the vertebral plate assembly is implanted; and channels individually traversing through the plurality of anchor members and adapted to receive means for securing the vertebral plate assembly to the superior and inferior vertebral bodies, wherein the channels traverse at angles aligned to the corners of the anterior cortex faces and vertebral endplates of the superior and inferior vertebral bodies when the plate assembly is implanted.

Further embodiments are directed to methods of implanting a vertebral plate assembly partially within an intervertebral space between superior and inferior vertebral bodies having anterior cortex faces and vertebral endplates, comprising providing a vertebral plate assembly having (i) a posterior surface and an anterior surface; (ii) a plurality of anchor members coupled to the anterior surface of the plate section; and (iii) channels individually traversing through the plurality of anchor members and adapted to receive means for securing the plate assembly to the superior and inferior vertebral bodies; inserting the posterior surface of the vertebral plate into the intervertebral space and into an implantable position, such that the anterior surface of the vertebral plate is external to the intervertebral space, the plurality of anchor members abut against the anterior cortex faces, and the channels traverse at angles aligned to the corners of the anterior cortex faces and vertebral endplates of the superior and inferior vertebral bodies; and inserting means for securing the plate assembly through the channels and into the superior and inferior vertebral bodies, through the corners of the anterior cortex faces and vertebral endplates.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Embodiments of the present invention are described below with reference to the above described Figures. It is, however, expressly noted that the present invention is not limited to the embodiments depicted in the Figures, but rather the intention is that modifications that are apparent to the person skilled in the art and equivalents thereof are also included.

Figures 1, 2A:
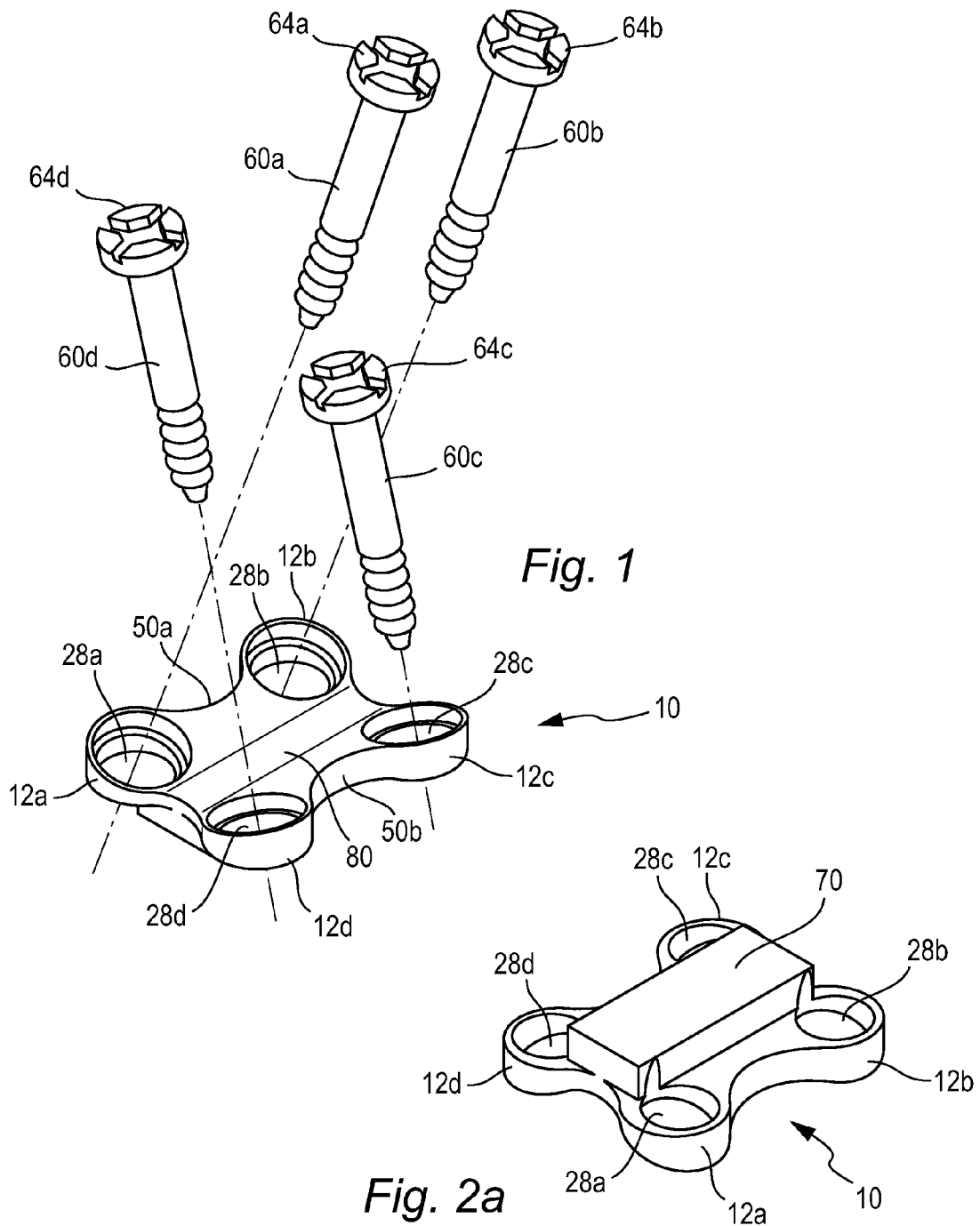
FIG. 1 is a perspective view of the anterior face of a vertebral plate assembly.
FIG. 2a is a perspective view of the posterior face of a vertebral plate assembly.
Figure 2B:
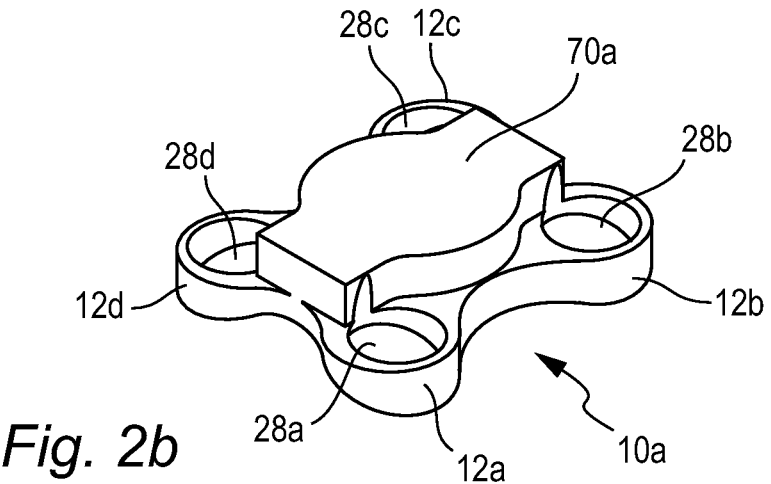
FIG. 2b is a perspective view of a posterior face of an alternative vertebral plate.
Figure 2C:
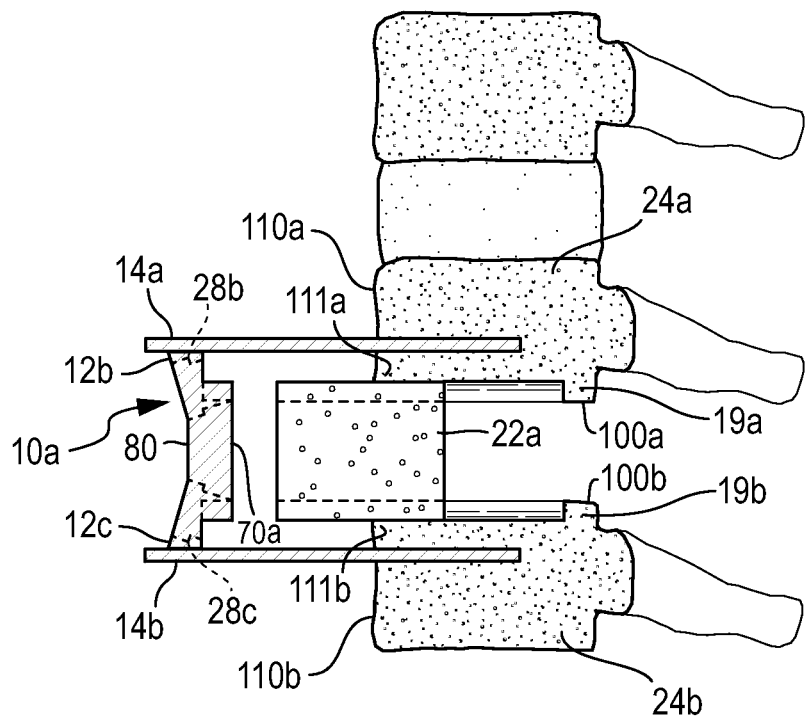
FIG. 2c is a lateral view of the alternative vertebral plate and alternative graft being aligned into an intervertebral space.
Figure 2D:
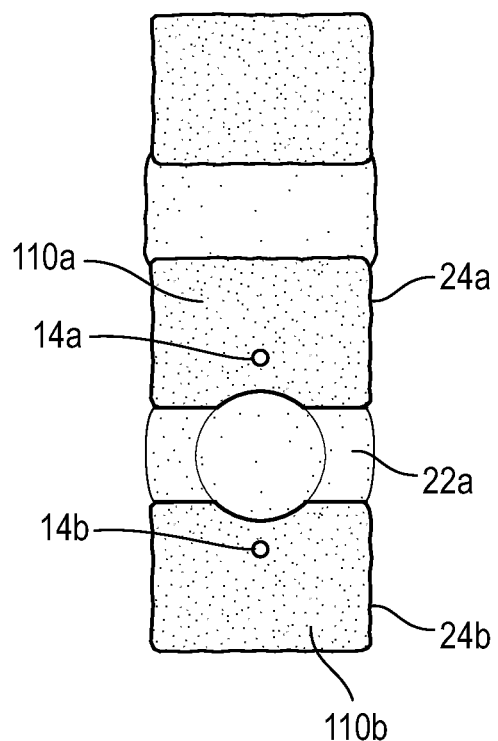
FIG. 2d is an anterior view of an alternative graft implanted into intervertebral space.
Figure 3:
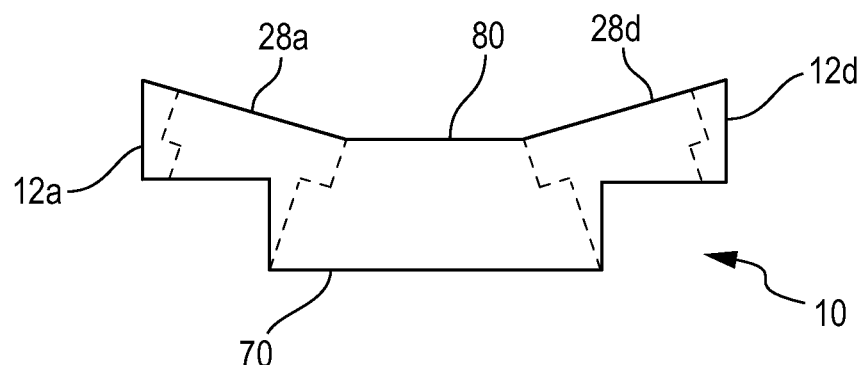
FIG. 3 is a side view of a vertebral plate assembly.
Figure 4:
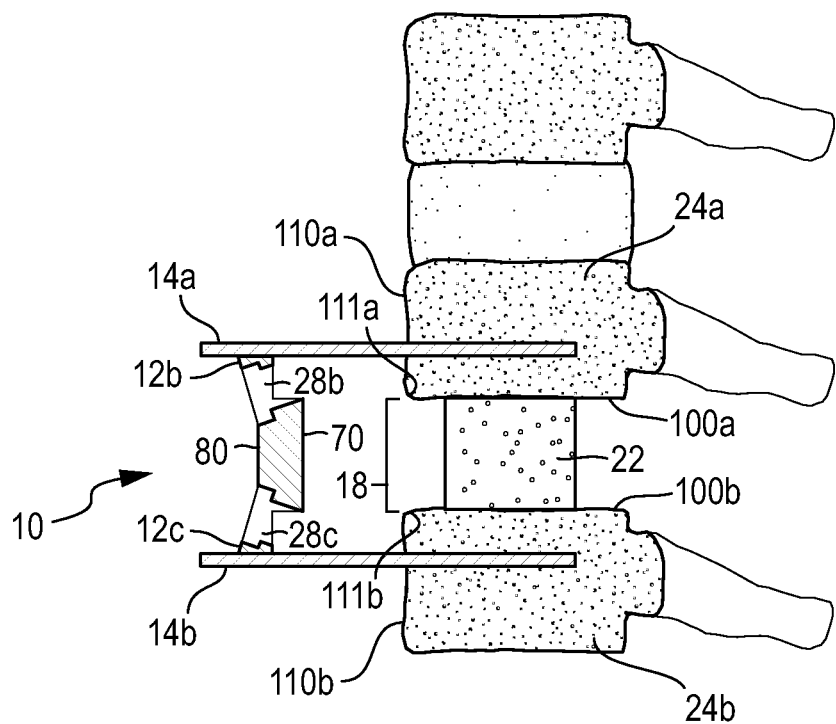
FIG. 4 is a lateral view of a vertebral plate assembly being aligned into an intervertebral space with a graft.
Figure 5:
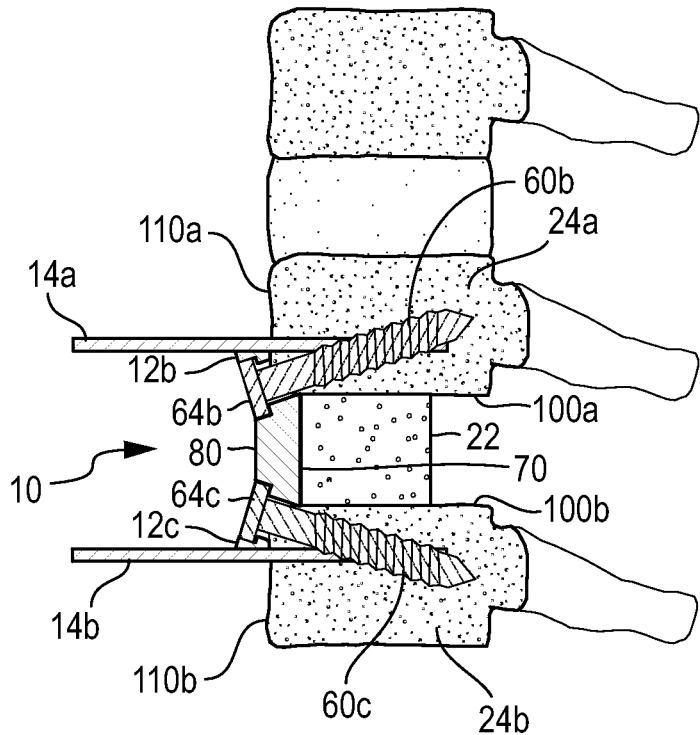
FIG. 5 is a lateral view of a vertebral plate assembly implanted into the intervertebral space.
Figure 6:
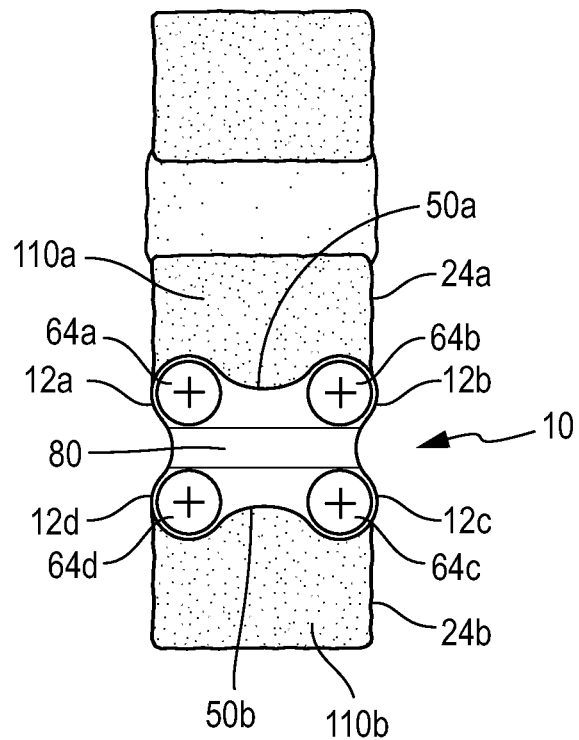
FIG. 6 is an anterior view of an implanted vertebral plate assembly.
Figure 8:
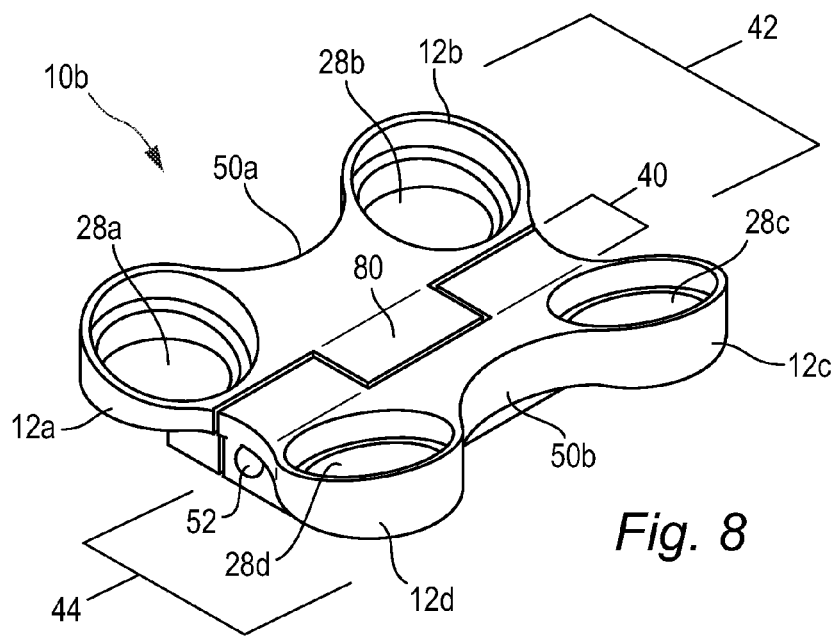
FIG. 8 is a perspective view of the anterior face of a hinged vertebral plate assembly in an unflexed position.
Figure 9:
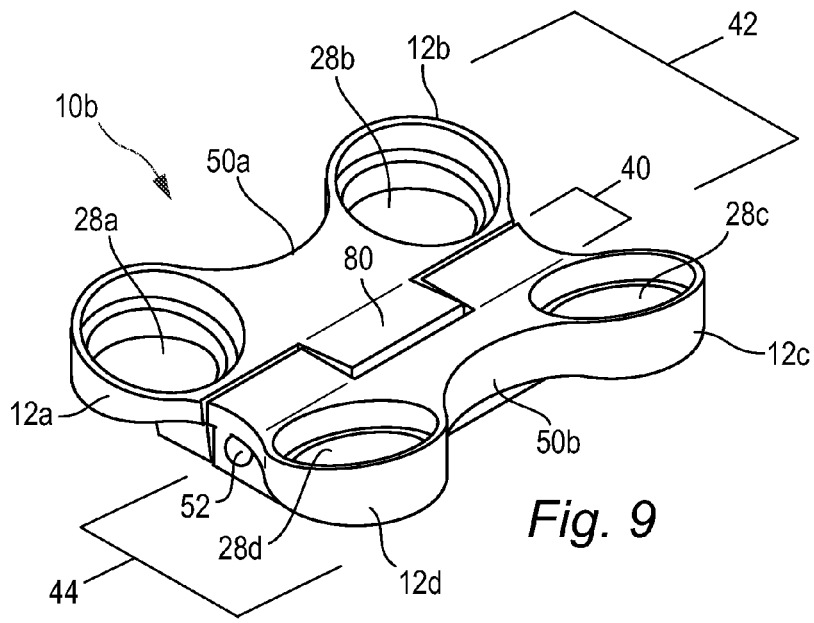
FIG. 9 is a perspective view of the anterior face of a hinged vertebral plate assembly in a flexed position.
Figure 9A:
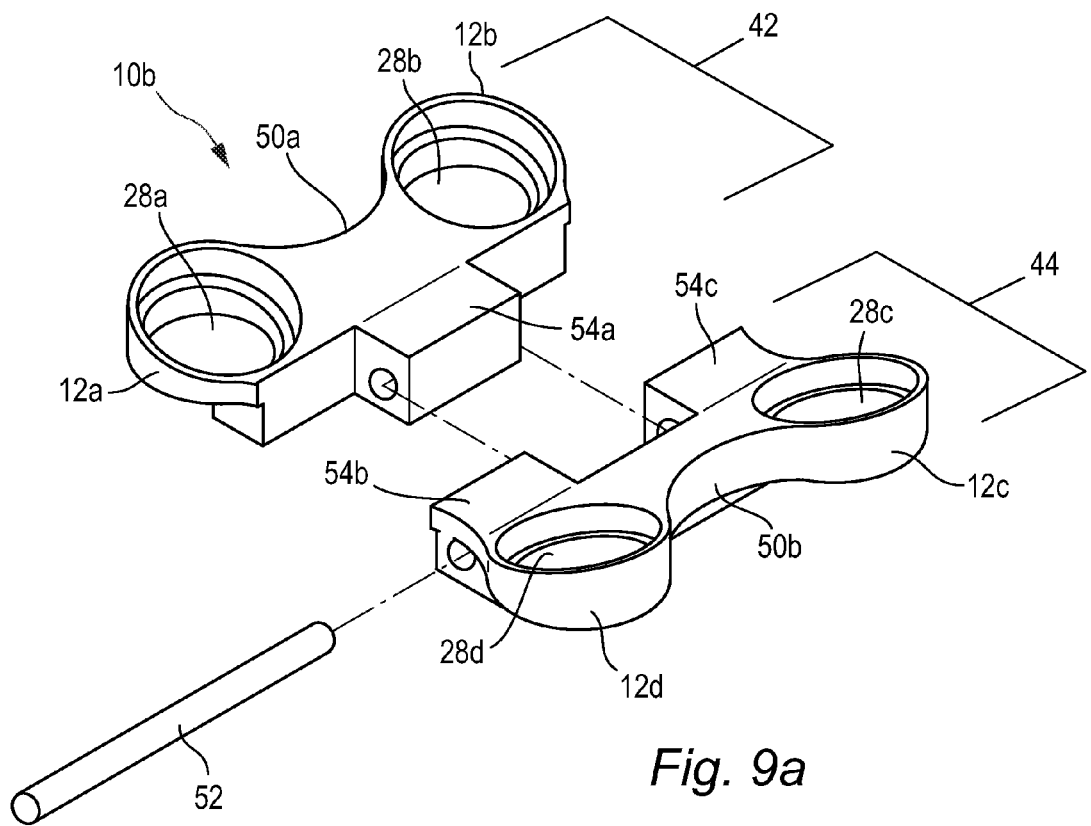
FIG. 9a is an exploded view of the anterior face of a hinged vertebral plate assembly.
Figure 10:
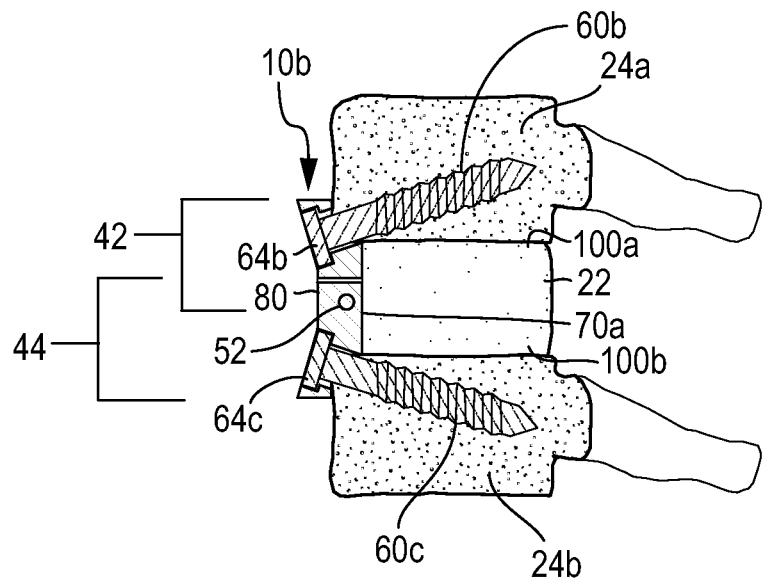
FIG. 10 is a lateral view of an implanted hinged plate assembly.
Figure 11:
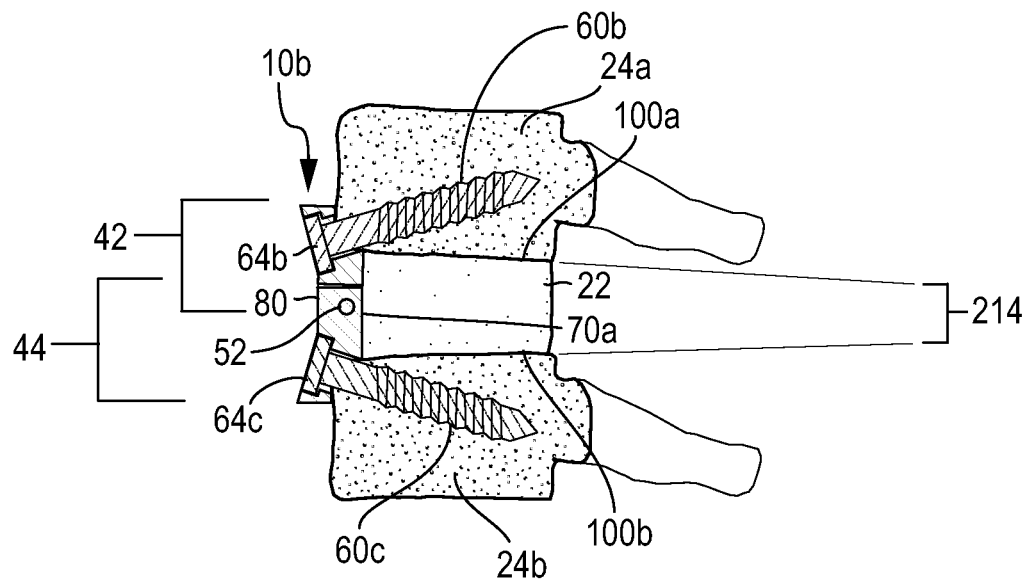
FIG. 11 is a lateral view of an implanted hinged plate assembly flexing toward the vertebral column.

FIGS. 1, 2a, and 3 show an unhinged vertebral plate assembly 10, FIG. 2b shows an alternative unhinged vertebral plate 10a having an alternative posterior face 70a, FIG. 2c shows an alternative vertebral plate 10a and alternative graft 22a being implanted, FIG. 2d shows anterior view of an alternate graft 22a implanted into an intervertebral space, FIGS. 4-6 show a vertebral plate assembly 10 being implanted, FIGS. 8-9 shown a hinged vertebral plate assembly 10b, and FIGS. 10-11 shown an implanted hinged plate assembly 10g. Methods provided herein for installing the non-hinged vertebral plate assemblies 10 and 10a can expressly be used for implanting the hinged vertebral plate assembly 10b. Unless stated otherwise, the term "vertebral plate assembly" as used herein generally relates to spinal implants, whether hinged or non-hinged, whether having a rectangular posterior face 70 or an alternative posterior face 70a, configured to be implanted partially internal and partially external to the intervertebral space 18 and further include a plurality of anchor members 12a-d. Accordingly, description directed to plates 10 having a rectangular posterior face 70 is also applicable to hinged plates 10b and alternative plates 10a having an alternative posterior face, such as in the shape of a rectangle with a circular middle that extends past the perimeter of the rectangle 70a.

According to preferred methods, a surgeon first removes the intervertebral disc (disectomy) and/or one or more vertebral bodies (corpectomy), or portions thereof, by using a distractor using techniques known in the art (not shown). In general, distractor pins 14a and 14b are individually fixed to vertebral bodies 24a and 24b respectively, which are positioned superior and inferior to the designated disc or section being removed. Typically, the distractor pins 14a and 14b are screwed into the vertebral bodies 24a and 24b. A distractor tool engages the exposed heads of the pins 14a and 14b and expands to mechanically separate the vertebral bodies 24a and 24b to allow the surgeon better access to the designated disc or section to be removed.

Distractors and methods of distracting are known in the art and any suitable one can be used with the teachings herein. One non-exclusive example of a distractor/retractor that can be used for separating vertebral bodies is disclosed in U.S. Pat. No. 7,494,463 to Daniel G. Nehls, which is hereby expressly incorporated by reference herein in its entirety. After the designated disc material and/or vertebral body are removed, a graft 22 can be inserted into the resulting space, using techniques and materials that are well known in the art.

Figure 4A:
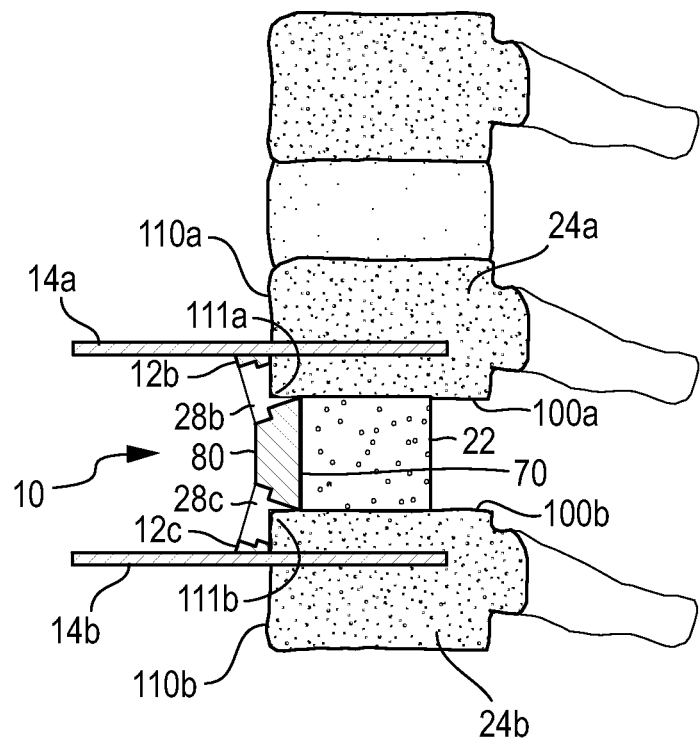
FIG. 4a is a lateral view of a vertebral plate assembly positioned into the intervertebral space with a graft.

As shown in FIGS. 4-6, preferred assemblies and methods are directed to using a low-profile, anterior vertebral plate assembly 10 to non-rigidly fix the superior 24a and inferior 24b vertebral bodies together after the graft 22 has been positioned into the intervertebral space 18. FIGS. 4-5 depicts distractor pins 14a and 14b opening superior and inferior vertebral bodies 24a and 24b to allow the vertebral plate assembly 10 to be aligned with and implanted into the intervertebral space 18. According to advantageous methods, the size of the plate assembly 10 is configured such that a portion of the plate assembly 10 is implanted within the intervertebral space 18 and a portion of the plate assembly 10 is implanted external to the intervertebral space 18. More specifically, a surgeon can implant the posterior face 70 of the plate assembly 10 into the intervertebral space 18, but not the anterior face 80. According to advantageous embodiments and as shown in FIGS. 4a and 5, when implanted, the anchor members 12a-d can be partially internal and partially external to the intervertebral space 18. The plate assemblies 10 herein can be implanted to fit snugly within the intervertebral space 18 to prevent slippage or unneeded movement.

Advantageously, after the vertebral plate assembly 10 has been positioned between the two vertebral bodies 24a and 24b, as shown in FIG. 4a, the surgeon can use the distractor tool (not shown) which is engaged with the distractor pins 14a and 14b to compress the intervertebral space 18 and more preferably the graft 22. Advantageously, the vertebral plate assembly 10 includes superior and inferior notches 50a and 50b, or grooves, concave or otherwise to allow the distractor pins 14a and 14b to enhance compression of the vertebral bodies 24a and 24b after the plate assembly 10 is positioned or implanted. This compression can allow the graft 22 to have better contact with the vertebral endplates 110a and 110b, and thus increase the chances of incorporation.

According to more specific embodiments, the plate assemblies 10 herein include a posterior face 70 that is configured to be positioned within the intervertebral space 18 and faces the graft 22 when implanted. When the plate assembly 10 is implanted, it is preferable that the posterior face 70 of the plate assembly 10 abuts the implanted graft 22 as shown in FIGS. 4a and 5 or comes substantially close to doing so. The surgeon can readily select, and/or shape the graft 22 to allow for more or less space for the plate assembly 10 within the intervertebral space 18, using any suitable method. Additionally different sized plate assemblies 10 can be made available to accommodate the size of the implanted graft 22 and the intervertebral space 18.

Additionally the plate assemblies 10 herein include an anterior face 80 that is external to the intervertebral space 18 and faces away from the implanted graft 22. FIG. 6 shows the anterior face 80 of an implanted plate assembly 10. The anterior face 80 should only protrude a small distance out from the intervertebral space 18 beyond the anterior faces 110a and 110b of the vertebral bodies 24a and 24b (See FIG. 4a). Preferably the anterior face 80 of the plate assembly 10 protrudes under 2 mm from the anterior faces 110a and 110b of the vertebral bodies 24a and 24b. Additionally, the height of the posterior face 70 is adapted or selected such that it advantageously does not traverse past the endplates 100a and 100b of the superior and inferior vertebral bodies 24a and 24b when implanted.

Preferably the plate assemblies 10 described herein are configured to be placed between two vertebral bodies 24a and 24b in the cervical or lumbar region of the spine and thus can be sized accordingly. As the plates assemblies 10 described herein are configured to be fitted partially into an intervertebral space 18, the methods herein are exclusively directed to anterior implantation within the vertebral column. Assemblies and methods directed to posterior vertebral implantation are expressly excluded herein. Preferred shapes of the plates and their posterior faces provided herein, include rectangular 70, square, rectangular with a circular middle that extends past the perimeter of the rectangle 70a, butterfly-shaped, oval, or other suitable shapes that comply with the teachings herein. According to alternative embodiments, the posterior face 70 of the plate assembly 10 can be in a different shape compared to the anterior face 80. Preferred vertebral plate assemblies 10 described herein can be made of any suitable and implantable material including titanium, surgical steel, aluminum, or other metal, polyether ether ketone (PEEK) and, carbon fiber, for example.

FIG. 2b shows an alternative vertebral plate 10a that includes a posterior face 70a shaped as a rectangular with a central circle. This particular shape of posterior face 70a is particularly useful for embodiments where the intervertebral space has been milled. More specifically and with reference to FIGS. 2c and 2d, a handheld mill can create a horizontal cylindrical bore in the middle of the intervertebral space. Preferably the bore does not traverse the entire distance of the vertebral bodies 24a and 24b such that upper and lower shelves 19a and 19b are created on the endplates 100a and 100b. These shelves 19a and 19b are advantageous in preventing the graft 22a from inadvertently dislodging posteriorly. An anterior view of the implanted alternative graft 22a is shown in FIG. 2d. This alternative graft 22a is preferably rectangular shaped with a central circle that aligns to the milled bore in the intervertebral space. The combination of the milled bore, shelving 19a and 19b, the alternative graft shape 22a help to establish a tight fit of the graft 22a into the intervertebral space. With continued reference to FIGS. 2c and 2d, the rectangular with a central circle shape of the posterior face 70a of the alternative plate 10a is preferably the same size and shape, or approximately so, of the anterior face of the alternative graft 22a.

Alternative shapes and methods to cylindrical milling are also contemplated for generating shelving in the intervertebral space, including rectangular chiseling for example. While the alternative shaped graft 22a is preferably used in the milled bore embodiment, the original graft 22, and/or vertebral plate 10 with the rectangular posterior face 70 can also be used with this embodiment or with vertebral shelving 19a and 19b.

According to further embodiments, the plate assemblies 10 provided herein also include one or more anchor members 12a-d. While preferred embodiments are directed to a plate assembly 10 having four anchor members 12a-d protruding at each corner of the anterior face 80, alternative numbers and positions of anchor members are also contemplated with the embodiments herein. 2, 3, 4, 5, and 6 anchor members, positioned along the anterior face 80 of the plate assembly 10 whether positioned intermittently, centrally, or in the corners, are readily contemplated herein. When the plate assembly 10 is implanted, one or more superior anchor members 12a and 12b abut against the junction 111a of the anterior face 110a and the endplate 100a of the superior vertebral body 24a. Similarly, one or more inferior anchor members 12c and 12d abut against the junction 111b of the anterior face 110b and the endplate 100b of the inferior vertebral body 24b, when the plate assembly 10 is implanted. Alternatively, 1, 3, or 4 superior anchor elements and 1, 3, or 4 inferior anchor members can be positioned on the plate assembly.

The vertebral plate assembly 10 preferably includes means for securely fastening to the vertebral bodies 24a and 24b. While the means for securely fastening can be positioned anywhere on the plate assembly 10, preferred positions are located within the one or more anchor members 12a-d. More specifically, the anchor members 12a-d can individually include a fastener channel 28a-d configured to allow the body of a fastening device 60a-d, such as a bone screw, bolt or nail, to pass through and into the bone. Washers, nuts, or other securing means can be used in conjunction with the fastening devices 60a-d, to ensure the plate assembly 10 is securely fastened to the vertebral bodies 24a and 24b. Preferably the fastener channels 28a-d are large enough for only the body of the fastening device 60a-d, such as screw bodies, but not the head or cap 64a-d of the fastening device (e.g., screw heads) to pass through. The fastener channels 28a-d can be sized to fit any desired vertebral fastening device, non-exclusively including screws, bolts, or nails.

According to preferred embodiments, when the one or more superior anchor members 12a and 12b are positioned against the anterior face 110a of the superior vertebral body 24a, their respective fastener channels 28a and 28b are configured to align with the junction, or corner 111a of the superior endplate 100a and the anterior face 110a of the superior vertebral body 24a. Likewise, when the one or more inferior anchor members 12c and 12d are positioned against the anterior face 110b of the inferior vertebral body 24b, their respective fastener channels 28c and 28d are configured to align with the junction, or corner 111*b*, of the inferior endplate 100*b* and the anterior face 110*b* of the inferior vertebral body 24*b*. As shown in FIG. 5, the above described alignment of the fastener channels 28*a-d* is advantageous in allowing the bodies 60*a-d* of the fastening devices to be secured within their respective vertebral body 24*a* and 24*b*, through the junction 111*a* and 111*b* of the anterior face 110*a* and 110*b* and its respective endplate 100*a* and 100*b*. Accordingly, the bodies 60*a-d* of the fastening devices are implanted at the same angle through the vertebral junctions 111*a* and 111*b* as the fastener channels 28*a-d* when the plate assembly 10 is finally positioned within the intervertebral space 18.

The above methods are advantageous because the junction 111*a* and 111*b* of a vertebral body's anterior face 110*a* and 110*b* and its respective endplate 110*a* and 110*b* is hard bone, and allows for stronger fixation by the body 60*a-d* of the fastening device. The bodies of the fastening devices 60*a-d* are expressly not implanted perpendicular to the anterior faces 110*a* and 110*b* (in a horizontal, anterior/posterior direction, or transverse plane) or the endplates 100*a* and 100*b* (in a vertical, superior/inferior direction, or a coronal plane) of their targeted vertebral bodies 24*a* and 24*b*.

Pilot holes (not shown) having a smaller diameter than the bodies of the fastening devices 60*a-d* can be drilled into the vertebral bodies 24*a* and 24*b* prior to securing the plate assemblies 10. Preferably the pilot holes would be made at the same angles through the junctions 111*a* and 111*b* of the anterior faces 110*a* and 110*b* and the endplates 100*a* and 100*b* as the fastener channels 28*a-d* when the plate assembly 10 is properly positioned within the intervertebral space 18. Alternatively, the bodies of the fastening devices 60*a-d* can be inserted directly into the vertebral bodies 24*a* and 24*b* without pilot holes. Templates and other aligning devices can also be used with the teaching herein to align the plate assemblies 10 and the fastening devices 60*a-d* into their proper positions.

Hinge Member

The plate assemblies described herein can either include a hinge member 40 or not. Those with skill in the art will readily recognize features and methods of implanting directed to non-hinged assemblies 10 and 10*a* above can be readily interchangeable with the hinged plate assemblies 10*b* described below, and are expressly included herein. According to additional embodiments, and as depicted in FIGS. 8-9, a second vertebral plate assembly 10*b* herein includes a hinge member 40 to allow the plate assembly 10*b* to flex, or angle towards the vertebral column at a limited angle. The flexing of the hinge member 40 towards the vertebral bodies 24*a* and 24*b* allows the graft 22, positioned within the disc space 18, to be under a compressive load, which enhances fusion.

Figure 8A:
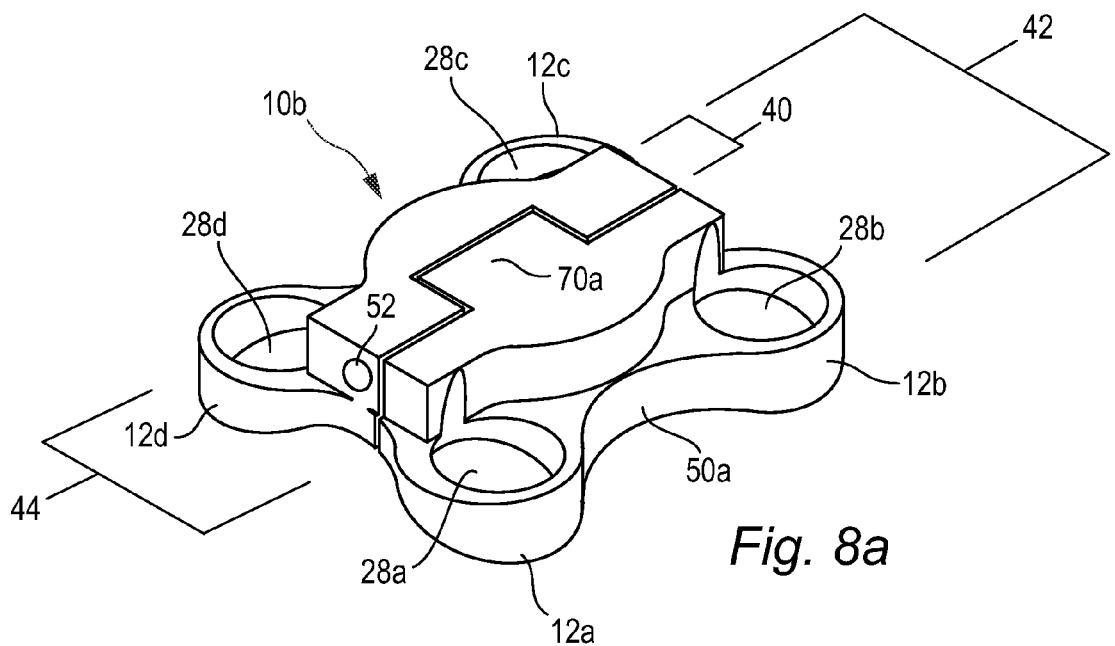
FIG. 8a is a perspective view of the posterior face of a hinged vertebral plate assembly in an unflexed position.

With reference to FIGS. 8-9, the hinge member 40 traverses laterally along the hinged plate assembly 10*b* thereby defining a superior plate section 42 and an inferior plate section 44. While in the figures, the superior and inferior plate sections 42 and 44 are different shapes, other suitable shapes (e.g., rectangles, semi-circles, semi-ovals, and the like), including the same shape can also be used with the teachings herein. FIGS. 8, 8*a*, and 10 show the plate assembly 10*b* in an unflexed position, where the superior plate section 42 and an inferior plate section 44 define a 180 degree angle, or substantially so. In contrast, FIGS. 9 and 11 show the hinged plate assembly 10*a* in a flexed position, where the posterior face 70*a* of the superior plate section 42 and the inferior plate section 44 define an angle of less than 180 degree angle.

Hinge members 40 are readily known in the art, and any suitable type of hinge can work with the teachings herein. In general, a hinge member 40 includes a lateral axis of rotation that couples both the superior and anterior sections 42 and 44 of the vertebral plate assembly 10*b* and allows limited pivotal rotation. Hinge members 40 can advantageously include one or more pivot pins, knuckles, barrels, springs, prongs, and the like to allow limited flexion towards the vertebral column. As one non-limiting example, FIG. 9 shows an exploded hinged plate assembly 10*b* that includes a pivot pin 52 configured to traverse through a plurality of alternating superior and inferior knuckles 54*a*-54*c*. More specifically the superior section 42 includes a central knuckle 54*a* configured to be sandwiched by two knuckles 54*b* and 54*c* on the inferior section 44 when the vertebral plate assembly 10*b* is assembled. This configuration can readily be reversed, and more knuckles can also be used if so desired. Advantageously, each knuckle 54*a-c* includes aligning channels configured to allow the pivot pin 52 to pass through, thereby laterally bisecting the vertebral plate assembly 10*b*.

According to preferred teachings, the hinged plate assembly 10*b* includes means advantageously configured to prevent extension of the superior and inferior plate sections 42 and 44 away from the vertebral body beyond 180 degrees. Additionally, the hinged plate assembly 10*b* can also include means to prevent excessive pivotal rotation or flexion towards the vertebral bodies 24*a* and 24*b*. More specifically, the posterior faces 70*a* of the superior and inferior plate sections 42 and 44 are configured to allow flexion towards each other at an angle less than 180 degrees. According to even more specific embodiments, the posterior faces of the superior and inferior plate sections 42 and 44 only permitted very limited flexion towards each other, such that when flexed, the angle degree is about 172 degree, or any of the following ranges: 170-175 degrees, 160-175 degrees, or 171-174 degrees, or substantially so. As those with skill in the art will readily appreciate, these limitations on the angle of pivotal rotation can be done non-exclusively through the use of stops, or other suitable means coupled to the hinged plate assembly 10*b*.

Figure 7:
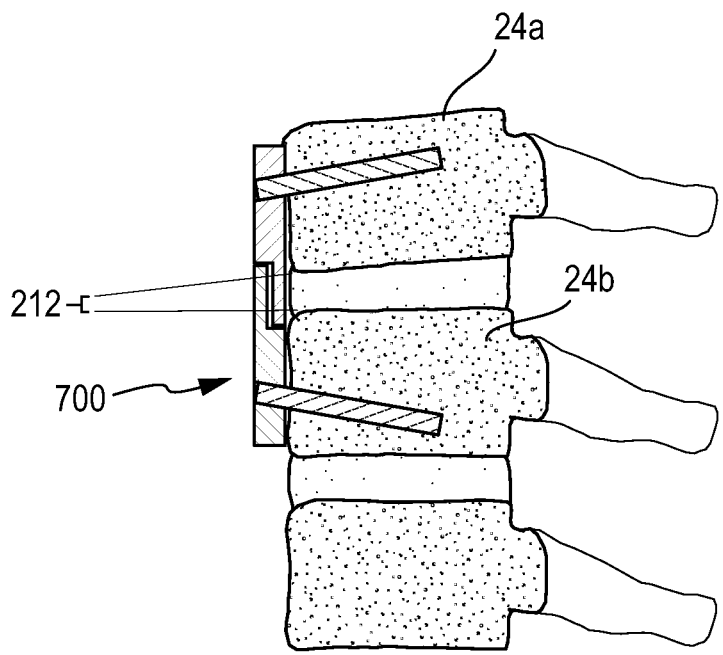
FIG. 7 is a lateral view of a prior art compressible plate causing kyphosis.

Advantageously, the hinge member 40 prevents the deformity known as kyphosis, or forward angulation, of the spine and encourages the natural lordotic or inward curvature, of cervical and lumbar regions of the vertebral column. FIG. 7 shows a prior art shortening plate 700 that can lead to kyphosis as shown in the forward angle 212 of the superior and inferior vertebral bodies 24*a* and 24*b*. In contrast, FIG. 10 shows a hinged plate assembly 10*b* implanted after a graft 22 has been inserted into the intervertebral space 18. When initially secured to the vertebral bodies 24*a* and 24*b*, the upper and lower plate sections 42 and 44 are in alignment at 180 degrees, or substantially so. With reference to FIG. 11, as the graft 22 is compressed by the superior and inferior vertebral bodies 24*a* and 24*b*, the upper and lower plate sections 42 and 44 flex towards each other slightly, thereby preventing kyphosis, and allowing for a preferred degree of lordosis 214 in the vertebral column. While FIGS. 10 and 11 show a non-milled intervertebral space, without shelves, the hinged plates 10*b* provided herein can readily be used with milled shelves.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

What is claimed is:

1. An interbody graft and a vertebral plate assembly adapted to be permanently implanted partially within an intervertebral space between superior and inferior vertebral bodies each having an anterior cortex face, and a vertebral endplate, the vertebral plate assembly comprising:

an anterior vertebral plate portion;
a posteriorly positioned insert portion having a posterior surface configured to fit within the intervertebral space and that abuts against an anterior surface of the interbody graft, and the anterior vertebral plate portion having an anterior surface that extends superiorly and inferiorly past a height of the insert portion;
a laterally traversing hinge member that defines superior and inferior sections of the vertebral plate assembly, including a superior posterior surface and an inferior posterior surface of the insert portion, wherein the hinge member is configured to allow after implantation limited flexion of the superior posterior surface and the inferior posterior surface of the insert portion towards each other to a flexed position to create a minimum angle between the superior posterior surface and the inferior posterior surface, wherein the minimum angle is between 165-175 degrees;
a plurality of anchor members coupled to the anterior surface of the anterior vertebral plate portion wherein the plurality of anchor members are configured to abut against the anterior cortex faces of the superior and inferior vertebral bodies when the vertebral plate assembly is implanted; and
channels individually traversing through the plurality of anchor members and adapted to receive means for securing the vertebral plate assembly to the superior and inferior vertebral bodies, wherein the channels traverse at angles aligned to corners at junctions between the anterior cortex face and vertebral endplate of each of the superior and inferior vertebral bodies when the plate assembly is implanted.

2. The vertebral plate assembly of claim 1, wherein the posterior surface of the insert portion and the anterior surface of the anterior vertebral plate portion are planar, or substantially so.

3. The vertebral plate assembly of claim 2, wherein the posterior surface of the insert portion and the anterior surface of the anterior vertebral plate portion are configured to be perpendicular, or substantially so, to the superior and inferior vertebral endplates when implanted.

4. The vertebral plate assembly of claim 1, wherein the hinge member is configured to prevent extension beyond 180 degrees of the superior and inferior sections away from the superior and inferior vertebral bodies after implantation.

5. The vertebral plate assembly of claim 1, wherein the plurality of anchor members includes four anchor members positioned at corners of the anterior surface of the anterior vertebral plate portion.

6. The vertebral plate assembly of claim 1, wherein the hinge member comprises one or more members selected from the group consisting of: pivot pins, knuckles, barrels, springs, and prongs.

7. The vertebral plate assembly of claim 1, wherein the hinge member comprises a pivot pin and knuckles.

8. The vertebral plate assembly of claim 1, wherein the hinge member laterally traverses across the entire superior and inferior sections of the vertebral plate assembly.

9. A method of permanently implanting an interbody graft and a vertebral plate assembly partially within an intervertebral space between superior and inferior vertebral bodies having anterior cortex faces and vertebral endplates, comprising:
providing the interbody graft and the vertebral plate assembly having:
(i) an anterior vertebral plate portion;
(ii) a posteriorly positioned insert portion having a posterior surface configured to fit within the intervertebral space and that abuts against an anterior surface of the interbody graft, and the anterior vertebral plate portion having an anterior surface that extends superiorly and inferiorly past a height of the insert portion;
(iii) a laterally traversing hinge member that defines superior and inferior sections of the vertebral plate assembly, including a superior posterior surface and an inferior posterior surface of the insert portion, wherein the hinge member is configured to allow after implantation limited flexion of the superior posterior surface and the inferior posterior surface of the insert portion towards each other to a flexed position to create a minimum angle between the superior posterior surface and the inferior posterior surface, wherein the minimum angle is between 165-175 degrees;
(iv) a plurality of anchor members coupled to the anterior surface of the anterior vertebral plate portion wherein the plurality of anchor members are configured to abut against the anterior cortex faces of the superior and inferior vertebral bodies when the vertebral plate assembly is implanted; and
(v) channels individually traversing through the plurality of anchor members and adapted to receive means for securing the plate assembly to the superior and inferior vertebral bodies wherein the channels traverse at angles aligned to corners at junctions between the anterior cortex face and vertebral endplate of each of the superior and inferior vertebral bodies when the plate assembly is implanted;
inserting the posterior surface of the insert portion into the intervertebral space and into an implantable position, such that the anterior surface of the anterior vertebral plate portion is external to the intervertebral space, the plurality of anchor members abut against the anterior cortex faces, and the channels traverse at the angles aligned to the corners at the junctions between the anterior cortex faces and vertebral endplates of the superior and inferior vertebral bodies; and
inserting the means for securing the plate assembly through the channels and into the superior and inferior vertebral bodies, through the corners at the junctions between the anterior cortex faces and vertebral endplates.

10. The method of claim 9, further comprising implanting the graft into the intervertebral space prior to inserting the posterior surface of the insert portion into the intervertebral space.

11. The method of claim 10, further comprising milling in a posterior direction a central, cylindrical bore in the intervertebral space to create shelves on the endplates of the vertebral bodies configured to prevent posterior dislodgement of the graft.

12. The method of claim 11, wherein the posterior surface of the insert portion is the same shape and size of the intervertebral space and cylindrical bore, or substantially so.

13. The method of claim 9, further comprising applying mechanical pressure to compress the superior and inferior vertebral bodies towards each other after the graft and the vertebral plate assembly have been inserted into the intervertebral space and into the implantable position.

14. The method of claim 9, wherein the posterior surface of the insert portion and the anterior surface of the anterior vertebral plate portion are planar, or substantially so.

15. The method of claim 14, wherein the posterior surface of the insert portion and the anterior surface of the anterior vertebral plate portion are configured to be perpendicular, or substantially so, to the superior and inferior vertebral endplates when implanted.

16. The method of claim 9, wherein the plurality of anchor members includes four anchor members positioned at corners of the anterior surface of the anterior vertebral plate portion.

* * * * *